United States Patent [19]

Osawa

[11] Patent Number: 4,541,419
[45] Date of Patent: Sep. 17, 1985

[54] SURGICAL CORSET

[76] Inventor: Masakazu Osawa, 34-14, Kameido 9-chome, Koto-ku, Tokyo-to, Japan

[21] Appl. No.: 621,671

[22] Filed: Jun. 18, 1984

Related U.S. Application Data

[63] Continuation of Ser. No. 465,905, Feb. 14, 1984, abandoned, which is a continuation of Ser. No. 343,757, Jan. 28, 1982, abandoned, which is a continuation of Ser. No. 191,994, Sep. 29, 1980, abandoned, which is a continuation of Ser. No. 86,710, Oct. 22, 1979, abandoned, which is a continuation of Ser. No. 852,747, Nov. 8, 1977, abandoned.

[30] Foreign Application Priority Data

Nov. 20, 1976 [JP] Japan .................. 51-139914

[51] Int. Cl.[4] .................................. A61F 5/02
[52] U.S. Cl. .................................. 128/78
[58] Field of Search ................ 128/78, 68; 2/44

[56] References Cited

U.S. PATENT DOCUMENTS

| 6,680 | 8/1849 | Davis | 128/78 |
|---|---|---|---|
| 129,202 | 7/1872 | Zachos | 128/78 |
| 344,639 | 6/1886 | Dewees | 128/78 |
| 976,564 | 11/1910 | Goodson | 128/78 |
| 2,453,370 | 11/1948 | Hittenberger | 128/78 |
| 2,796,866 | 6/1957 | Cohen | 128/78 |
| 2,828,737 | 4/1958 | Hale | 128/78 |
| 3,771,513 | 11/1973 | Velazquez | 128/78 |
| 3,945,376 | 3/1976 | Kuehnegger | 128/78 |

FOREIGN PATENT DOCUMENTS 103713 6/1899 Fed. Rep. of Germany ........ 128/78

Primary Examiner—Gene Mancene
Assistant Examiner—C. W. Shedd
Attorney, Agent, or Firm—Brisebois & Kruger

[57] ABSTRACT

A surgical corset including a shoulder section to be applied to the shoulders and having shoulder bands, a waist section to be applied to the waist, of which both the side margins are extended forwards to form supporting portions; a back section to be applied to the back and connecting the shoulder section and the waist section. A plurality of fasteners on both sides of the outer surface of the back section are spaced at a distance corresponding respectively to an aliquot of the whole length of the back section. Elastic straps are removably mounted along and on the back section by adjacent ones of the fastening members. This provides a surgical corset which is more conventionally and comfortably worn due to its elastic structure.

8 Claims, 5 Drawing Figures

SURGICAL CORSET

This is a continuation, of application Ser. No. 465,905, filed Feb. 14, 1984 now abandoned; which was a continuation of Ser. No. 343,757 filed Jan. 28, 1982 now abandoned; which was a continuation of Ser. No. 191,994, filed Sept. 29, 1980 now abandoned; which was a continuation of Ser. No. 086,710, filed Oct. 22, 1979 now abandoned; which was a continuation of Ser. No. 852,747, filed Nov. 8, 1977 now abandoned.

BACKGROUND OF THE INVENTION

This invention is related to Application No. 139914/Sho. 51, filed Nov. 20. 1976, and No. 92278/Sho. 51, filed Aug. 4, 1976 and their disclosures are incorporated herein by reference.

The present invention relates to a surgical corset for fixing the vertebral region, correcting the vertebral column to a normal condition and straightening backsinus or curvature of the spine, and in diseases of the vertebral column, the intervertebral discs or the like.

Heretofore, for treating diseases of the vertebral column, the intervertebral discs or the like, corsets have been employed in such a manner that the above-mentioned regions to be treated are merely wholly enclosed and fixed by the corsets, but problems such as pain of the patient when wearing the corset, weakening of the muscles of the spine caused by wearing it for a long time, etc. have arisen. Thus prior corsets have not been satisfactory. Further the above-mentioned conventional supporting or correcting corsets have the drawback that the extent of support or bracing cannot be varied with the condition of the disease.

SUMMARY OF THE INVENTION

The present invention provides:
a surgical corset comprising
a shoulder section to be applied to the shoulders, and having connecting bands;
a waist section to be applied to the waist, of which both the side margins are extended forwards to form supporting portions;
a back section to be applied to the back, connected to the lower margin of the shoulder section and also connected to the upper margin of the waist section; and
a plurality of elastic members, each having a length corresponding to an aliquot of the whole length of the back section, and placed along both sides of the outer surface of the back section, and removably secured to the back section.

An object of the present invention is to provide a surgical corset for supporting and retaining the vertebral column and the intervertebral discs, which enables varying its fixing or supporting extent depending upon the condition of the disease of the back.

Another object of the present invention is to provide a surgical corset capable of varying the extent of support of the vertebral column, and/or the intervertebral discs depending upon the condition of the disease.

Other objects will be apparent from the following description.

DETAILED DESCRIPTION OF THE INVENTION

Figure 1:
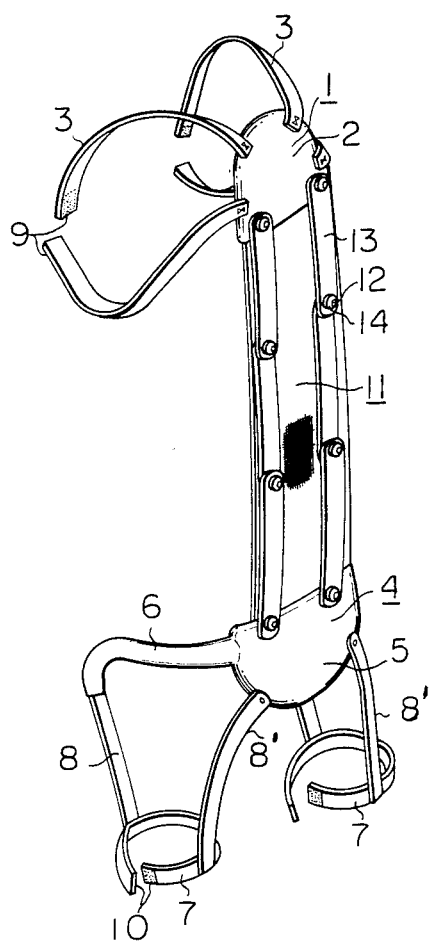
FIG. 1 is a perspective view of one preferred embodiment of the present invention.

One embodiment of the present invention will now be described referring to FIGS. 1, 2 and 3 of the accompanying drawings.

In these figures, numeral 1 shows a shoulder member or section to be applied onto the shoulders, consisting of a body sheet 2 of a rigid synthetic resin material, connected to a pair of right and left arm fitting bands or shoulder straps 3, 3.

Next, numeral 4 shows a waist member or section to be applied onto the waist, consisting of a body sheet 5 of a rigid synthetic resin, having at its side margins, a pair of right and left supporting portions 6, 6, respectively, of a semirigid synthetic resin, front bands 8 having their upper ends secured to the tips of support portions 6, 6, respectively, and their lower ends secured to the front of the respective leg bands 7, 7, rear bands 8', 8', having upper ends secured to side margins of body sheet 5, respectively, and lower ends secured to the rear of leg bands 7, 7, respectively. The leg bands 7, 7 comprise femoral region-binding bands 7, 7. These femoral region-binding bands 7, 7 and the above-mentioned shoulder fitting bands 3, 3 are furnished midway with a portion capable of being secured and released by a connecting means 9, 10 such as magic tape, VELCRO, or the like, fixed to opposed surfaces of these bands.

Next, numeral 11 shows a sheet which consistutes a back section to engage the back and which can be an elongated sheet of cloth or synthetic resin material, preferably stretchably longitudinally, which is fixed by sewing, at its upper end, to the shoulder member 1, and is fixed by sewing, at its lower end to the waist member 4. On the outer surface of this back sheet 11 are a plurality of spaced apart button fastening members 12 along both the sides of the sheet. Connected between these fastening members 12 are vertical elastic straps or plates 13. Each of the elastic straps 13, has holes at both ends to receive adjacent upper and lower fastening members 12. Straps 13 are removably fixed by press on metallic fastener means 14 which fit over the fastening memebers 12. Further, each of these elastic straps 13, is adjusted and fixed so as to provide a required tension, for example, by placing a single strap at a certain location, and a plurality of straps at another location between the various fastening members 12.

The above-mentioned elastic straps 13 employed in the present invention, can be belt-shaped flat rubber, a rubber sheet consisting of a rubber-containing tape, a leaf spring or the like. Further, as the above-mentioned elastic straps 13, a leaf spring 15 having a flat surface, but corrugated along the side margins can be used, spring 15 has staggered notches 15a on the right and left sides, and threaded openings 15b can be provided at each end, as shown in FIG. 3. The elastic straps 13 can also be bundled piano wires (not shown).

Figure 2:
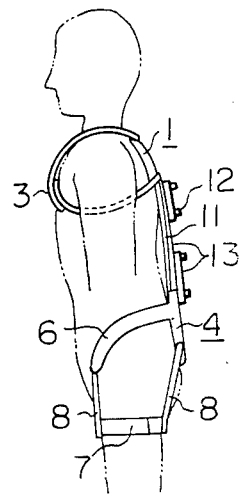
FIg. 2 is a side view in elevation showing a patient fitted with the corset of FIG. 1.
Figure 3:
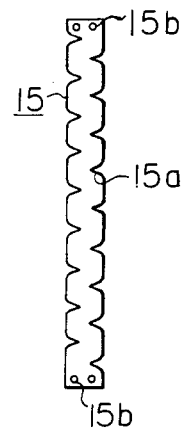
FIG. 3 is a plan view of another embodiment of the elastic member employed for the corset of the present invention.

To attach the corset having the above-mentioned structure, of the present invention, to the wearer's body as shown in FIG. 2, the shoulder member 1 is applied to the shoulder region, and the shoulder bands 3, 3 are extended under the arms and over the shoulders, and are secured. Then while the waist member 4 is drawn down against the elastic force of the elastic straps 13, waist member 4 is fixed by securing the femoral region-binding bands 7, 7 around the thighs so that the supporting portions 6, 6 of the member 4 are located on the lumbar bone.

As mentioned above, the present invention resides in a surgical corset obtained by forming members, to re-form the back region of the patient along and in contact with the back, by placing a number of elastic straps or plates 13, in a state of tension, on the surface of the sheet 11 applied to the back which is a sheet capable of being stretched to a certain extent upwards and downwards. Thus, this corset, in contrast to the conventional rigid corsets having no elasticity, functions so that the shoulder region is always drawn backwards by means of a soft or weak elastic force (spring force), and hence it is superior in efficiency. Further, since the elastic plates 13, are employed, there is little restriction, and motions of each region are not obstructed. Furthermore, the waist member 4 is retained at a location above the lumbar bone, and since it does not have elements tightening on the abdominal region, etc., it is comfortable.

Further, with regard to the elastic straps or plates 13, by optionally varying the number of plates between the various fastening members 12, it is possible to set the elastic force or traction in advance, to the strength necessary for fixing the waist region and the back region of the patient, or for supporting the upper part of the body suffering from rounded back, tortoise back, etc. (back-sinus or curve of spine), whereby the elastic plates are very effective.

Further, the corset of the present invention has the superior advantage that, by varying the number of the elastic plates, it is possible to vary its extent of correction according to the condition of the disease.

Next, another embodiment of the present invention will be described referring to FIGS. 4 and 5.

Figure 4:
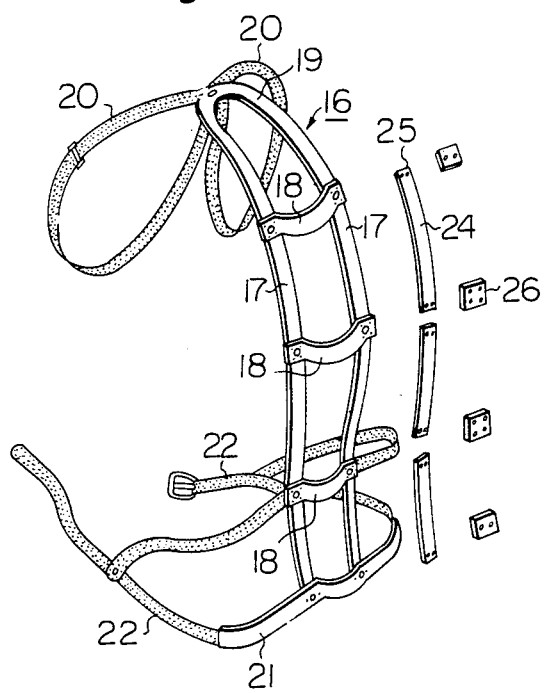
FIG. 4 is a perspective view of another embodiment of the corset of the present invention.
Figure 5:
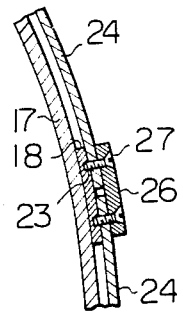
FIG. 5 is an enlarged view in section of a part of the elastic member of the embodiment of FIG. 4, showing its fastening.

In FIGS. 4 and 5, numeral 16 shows a frame consisting of two spaced parallel elongated straps or plates 17, 17 formed from elastic synthetic resin, etc., and connected together by a plurality of rigid transverse spacers 18, into a ladder form. At the upper part of the frame 16 is an inverted U-shaped shoulder section 19, integral with straps 17, 17. Fixed on the upper end of section 19 is a pair of right and left, adjustable ring-form should belts 20, 20. Fixed to the lower end of straps 17, 17 is a member 21 forming a waist section to be applied to the waist, and of a rigid synthetic resin or the like. Member 21 has connected to both ends thereof, fitting bands 22, 22 which can be stretchable and the length of which is adjustable by a buckle. At the locations where the spacers 18, and shoulder member 19 to be applied onto the shoulder are fixed to the frame 16, there are provided threaded openings 23, for securing separately provided elastic straps or plates 24. Straps 24 are overlaid along the frame, over the respective spacers 18. As shown in FIG. 5, one elastic strap or a plurality of elastic straps 24, overlaid on each other, can be connected between the spacers 18. At both ends of the elastic plates 24 are screw holes 25, and these ends are secured with small screws which extend through clamp plates 26, and into the threaded openings 23. The resulting whole is fixed by the small screws. In addition, the elastic plates 24 can be like spring 15 of FIG. 3, or can be bundled piano wires.

The corset of this second embodiment can be used in the same manner as in the first embodiment, and the same effectiveness is exhibited.

As many apparently widely different embodiments of this invention may be made without departing from the spirit and scope thereof, it is to be understood that the invention is not limited to the specific embodiments thereof except as defined in the appended claims.

What is claimed is:

1. A surgical corset comprising:
   a shoulder section to be applied to the shoulders, and having shoulder fitting bands;
   a waist section to be applied onto the waist, said waist section having side margins both of which extend forward to form forward supporting portions;
   a back section to be applied onto the back, said back section connecting a lower portion of said shoulder section and to said waist section;
   elongated elastic members, each having a length corresponding to an aliquot of the whole length of said back section, and placed on an outer face of and along both sides of said back section, said elastic members being longitudinally elastic to exert a vertical tractive force between the shoulder section and the waist section; and
   fastener means for removably connecting said elastic members to said back section.

2. A corset according to claim 1 wherein said shoulder section is rigid, and said waist section is rigid.

3. A corset according to claim 1 wherein said forward supporting portions of said waist section seat on the lumbar bone of the wearer.

4. A corset according to claim 1 wherein said shoulder section is flexible, and said waist section is rigid.

5. A surgical corset according to claim 1 wherein said shoulder fitting bands extend forwardly from the shoulder section; said waist section comprises femoral region connecting bands attached to respective lower ends of said forward supporting portions; said back section comprises an elongated sheet; and said elastic members have upper and lower ends each fastened to the back section by said fastener means.

6. A surgical corset according to claim 1 wherein said shoulder section and said back section form a single body comprised of vertical elastic straps in spaced apart parallel relation to each other, and connected by a plurality of transverse spacers; and
   waist bands attached to said forward portions of said waist section for securing the waist section to the user.

7. A surgical corset according to claim 1 wherein said longitudinally elastic members comprise rubber plates or straps.

8. A surgical corset according to claim 1 wherein said longitudinally elastic members comprise generally flat springs.

* * * * *